United States Patent [19]

Langner

[11] Patent Number: 6,008,027
[45] Date of Patent: Dec. 28, 1999

[54] ENTERIC POLYMER COATED CAPSULE CONTAINING DRIED BACTERIAL CULTURE FOR SUPPLYING LACTASE

[76] Inventor: Bruce J. Langner, 107 Monmouth Rd., Suite 202, West Long Branch, N.J. 07764

[21] Appl. No.: 08/896,210

[22] Filed: Jul. 17, 1997

[51] Int. Cl.[6] ............................. C12N 11/00; C12N 9/24; C12N 1/04; A61K 38/47
[52] U.S. Cl. ....................... 435/174; 424/451; 424/93.44; 424/93.45; 424/94.61; 435/177; 435/182; 435/200; 435/252.9; 435/253.4; 435/260
[58] Field of Search ................................ 424/93.4, 93.44, 424/93.45, 45.1, 94.61; 435/252.1, 252.9, 260, 174, 177, 182, 200, 253.4

[56] References Cited

U.S. PATENT DOCUMENTS

| | | | |
|---|---|---|---|
| 3,629,073 | 12/1971 | Cayle | 195/62 |
| 3,718,739 | 2/1973 | Cayle | 424/94 |
| 3,860,490 | 1/1975 | Guttag | 195/108 |
| 4,956,295 | 9/1990 | Sudama | 435/252.1 |
| 4,983,401 | 1/1991 | Eichel et al. | 424/473 |
| 5,478,570 | 12/1995 | Sunohara et al. | 424/463 |

*Primary Examiner*—David M. Naff
*Attorney, Agent, or Firm*—Norman E. Lehrer; Franklyn Schoenberg

[57] ABSTRACT

A lactase-containing preparation is prepared for use by mammals having a lactase deficiency. A dried bacterial culture containing lactase is mixed with a desiccant such as silicon oxide to stabilize water content of the dried culture. A unit dosage of the resultant stabilized dried bacterial culture is encapsulated in an ingestible capsule such as gelatin capsule. The capsule is coated with an enteric polymer, and the coated capsule is treated under vacuum pressure to remove oxygen and moisture. The treated coated capsule has an extended shelf-life at room and elevated temperatures, and provides lactase activity for at least 10 hours after ingestion. The dried bacterial culture may be in freeze dried form. Suitable bacterial cultures are *Lactobacillus acidophillus*, *Lactobacillus bulgaricus* and *Streptococcus thermophilus*.

8 Claims, No Drawings

ENTERIC POLYMER COATED CAPSULE CONTAINING DRIED BACTERIAL CULTURE FOR SUPPLYING LACTASE

BACKGROUND OF THE INVENTION

The present invention is directed to lactose and more particularly toward a lactase enzyme replacement capsule and a method of making the same.

Dairy foods are an important source of protein, riboflavin, and calcium for populations of the United States and Europe, and many people of those countries have a dairy disorder. Acquired lactase deficiency is the most common disorder of complex carbohydrate absorption in all populations. Up to seventy percent of the world's population has this disorder, resulting in gastrointestinal symptoms of excessive gas production, abdominal pain, bloating, and diarrhea after consumption of lactose and the by-products of lactose containing foods, e.g., milk, cheese, cakes, eggs, veal, and yogurt.

All mammals normally have a high level of lactase activity in the lining of the upper intestinal tract because they depend on lactose as the primary carbohydrate in their diet. However, lactase enzyme deficiency occurs naturally with age and genetically, or is secondary to disease states, such as inflammatory bowel disease.

Lactase enzyme replacement products, to date, have generally been useful as a replacement of the deficient enzyme for a short period of time prior to a meal or snack. Since this naturally occurring enzyme is required for digestion of most solid and liquid foods, its use is required by the individual during most periods of eating or snacking, to prevent the symptoms stated above. Failure to take the enzyme replacement products prior to or during a meal by people who experience lactase deficiency, results in poor absorption of the lactose which is then degraded by bacteria to lactic acid, short chain fatty acids and hydrogen gas. This, in conjunction with osmotic pressure created by the lactose, results in diarrhea, pain, gas, and bloating.

Lactose-hydrolyzing lactase enzymes are also known to be produced by various yeasts, bacteria, and fungi. Among the organisms useful in hydrolyzing lactose are *Saccharomyces fragilis, Torula cremoris, Lactobacillus bulgaricus, Aspergillus oryzae, Aspergillus flavus,* and *Aspergillus niger*. These organisms are cultured and used to prepare lactase enzyme preparations for lactase replacement products.

A few of the currently available lactase replacement products include, for example, LACTAID brand lactase available from Johnson & Johnson; DAIRY EASE available from Sterling Winthrop, a division of the Eastman Kodak Company; and LACTAID drops also available from Johnson & Johnson. LACTAID tablets utilize lactase of beta-D-galactosidase from the yeast *Aspergillus oryzae*. LACTAID drops utilize beta-D-galactosidase derived from *Kluyveromyces lactis* yeast. DAIRY EASE is available in caplets and drops. The caplets utilize lactase of beta-D-galactosidase from the yeast *Aspergillus oryzae* and the drops utilize beta-D-galactosidase derived from *Kluyveromyces lactis* yeast The lactase enzyme responsible for the degradation of lactose to glucose and galactose is rapidly metabolized after a meal or snack and within sixty minutes of ingestion before a meal is, for practical purposes, non-existent requiring additional dosing prior to the ingestion of a further meal or snack.

Bacid, another form of lactase replacement products available from Ciba, Self-Medication, Inc. in Woodbridge, N.J. are capsules containing not less than 5 million colonies of *Lactobacillus acidophillus* which produce lactase for the degradation of lactose. Two of such capsules must be taken prior to each meal/snack. The capsules are exceedingly sensitive at ambient temperatures and if not refrigerated, rapid death of the Lactobacillus cells results with subsequent ineffectiveness of the product.

Problems associated with various lactase enzyme replacement products are discussed, for example, in U.S. Pat. No. 3,718,739 to Cayle which discloses a method of administering an acid-active, acid-stable lactase enzyme preparation for the hydrolysis of lactose in acid media such as gastric fluids of lactase-deficient mammals. The lactase replacement preparation and treatment, however, does not provide a preparation in unit dosage form which has long acting capability nor is it impervious to elevated temperatures and moisture over long periods of time.

Accordingly, there exists a need for a dietary lactase replacement available in capsule and the like unit dosage form, containing *Lactobacillus acidophillus* or the like cultured strain, which is capable of sustaining activity for an extended period of time, e.g., a minimum of ten hours upon a single ingestion, and which exhibits suitable thermal resistance, thus allowing the lactase deficient user to supplement his/her diet at will with lactose containing food/liquid entities without any undesirable side effects of the same while permitting the storage and shipping of such preparations without loss of activity.

SUMMARY OF THE INVENTION

Accordingly, it is an object of the present invention to overcome the deficiencies of the prior art described above and to provide a method for making an enteric coated lactase replacement preparation in capsule and the like unit dosage form which includes a bacterial/fungal culture of lactase replacement enzymes mixed with stabilizing desiccants. The mixture is then placed in a gelatin capsule and banded. The capsule is then sealed with an enteric coating and placed in a vacuum chamber to remove oxygen and moisture. Such a vacuum treatment permits extended shelf life of the preparation at room and elevated temperatures.

It is another object of the present invention to provide a lactase replacement supplied in an enteric coated capsule dosage form suitable for ingestion by consumers which is capable of use as a lactase replacement which is effective after ingestion for extended periods of time, e.g., at least ten hours, preferably, up to twenty-four hours.

It is a further object of the present invention to provide lactase replacement in capsule form which is shelf stable and may be stored without loss of activity for extended periods under ambient conditions.

DETAILED DESCRIPTION OF THE PREFERRED EMBODIMENT

In accordance with the present invention a lactase replacement preparation in the form of a capsule that is readily ingestible by a human or animal and which is available to provide the desired lactase replacement for extended periods of time after ingestion, e.g., for at least ten hours and preferably to about twenty-four hours is provided. The lactase replacement capsule of the present invention is formed by using bacterial/fungal cultures, including, for example, *Lactobacillus acidophillus, Lactobacillus bulgaricus,* and *Streptococcus thermophilus* supplied in freeze dried colony form. The bacterial culture in powder form is mixed with stabilizing dessicants such as silicon oxide, silicon dioxide, microcrystalline cellulose, or redried starches and loaded in unit dosage gelatin capsules. The gelatin capsules are then banded and sealed with an aqueous enteric polymer coat using known capsule coating technique, such as an aromatic fluid bed coating, with a known polymer coating suspension such as Eudragit. The capsule is then placed in a chamber under a vacuum of approximately 55–70 microns for 24 to 144 hours, and preferably for 72 hours, using a vacuum pump.

The manufacture of the lactase replacement of the invention in unit dosage capsule form, using L. acidophillus as an example, will now be described. L. aciclophillus supplied in a freeze dried colony form containing an amount in the range of from about 50% weight percent to about 100% weight percent and preferably from about 90% weight percent to about 95% weight percent is mixed with silicon dioxide in proportions to provide from about 95% volume of L. acidophillus in a 250 mg capsule (minimum concentration about 250,000) mixed with 5% silicon dioxide. The encapsulated mixture is sealed with an aqueous enteric polymer coating using an Eudragit polymer. The capsule is then placed in a vacuum chamber at about 55–70 microns for seventy-two hours using a vacuum pump, thereby removing oxygen and moisture from the capsule.

Various experiments conducted where capsules were formed and enterically coated but not subjected to vacuum treatment to remove moisture resulted in capsules that did not survive at elevated temperatures (35° C. or higher) for extended periods. When desiccants were used along with vacuum suctioning, enzyme activity capsules survived elevated temperature (35° C.) and moisture levels for periods as long as 18 months, and even longer. Furthermore, it was found that using Eudragit for the enteric coat had several advantages over using other types of polymers for the coating. For example, this coating could be applied at low temperatures, such as 25° C., and it was possible to eliminate the use of the opadry coating steps typically used before. The elimination of these steps speeds the coating process, allowing less heat exposure per unit time.

The lactase replacement composition of the present invention also overcomes the disadvantages of currently available lactase replacement products in two significant ways. First, the capsule of the present invention provides a capsule form of replacement that has long acting capability after ingestion by preventing premature release of the bacterial culture. Secondly, the capsule provides an increased shelf life.

First of all, the lactase replacement capsule of the invention by utilizing a combination of desiccant within a capsule in conjunction with an enteric coating is sturdy enough to prevent stomach acid, such as hydrochloric acid, from destroying the capsule and prematurely releasing the bacterial culture. Once the capsule is opened in an elevated alkaline environment, e.g., the alkalinity of the small bowel, the culture is able to "implant" itself onto the small bowel, proliferate, and produce continual lactase replacement activity for the consumer for approximately 24 hours. Moreover, because the bacteria replacement capsule of the invention is capable of withstanding gastric acids and getting into the small intestine without destruction, the bacterial culture is present after 3–5 days from ingestion and is able to continue to produce lactase enzyme for the 3–5 days without the need for the individual to consume additional cultures. In general, individual serving size will initially require two capsules in the morning and two capsules ten hours later for seven days. After the seven days, the individual will require one to two capsules every twenty-four hours, depending upon the degree of lactose intolerance.

The cumulative effect of these microorganisms is to control the composition and metabolic activity of the intestinal microflora. This optimum balance has been associated with good nutrition and health. These organisms produce antibiotics, lower pH, promote oxidation reduction augmenting antimicrobial actions, and deconjugate bile acids in the intestinal tract exerting an influence on the presence of other types of bacteria. Studies indicate a cholesterol lowering property for coronary artery disease and biodegradation of nitrates implicated as a causative factor in colon cancer.

Secondly, the shelf life of the capsules is increased as a result of the use of drying agents, highly concentrated bacterial colony count, and exposure of the capsules to vacuum pressure over a set period of time. Variables resulting in the premature death of most bacterial cultures include elevated temperatures, low pH, elevated pressures, and elevated moisture levels. Small changes in moisture and temperature appear to be the most deleterious. In the present invention, the capsules have been found to withstand elevated temperatures, such as 35° C., and moisture levels as a result of the combination of the drying agent, high concentration of bacterial culture, and exposure to vacuum pressure. Therefore, the previous ineffectiveness of the bacterial culture after three to six months of shelf life, has been prolonged to eighteen months at room temperature and to four months at continuous elevated temperatures and to four months at continuous elevated temperatures and moisture. Competitive products have a 100% death rate after 24 hours at this elevated temperature.

The above is a general description of the present invention. The following examples are given for the purpose of illustration and are not intended in any way to limit the invention as claimed. Unless noted to the contrary, proportions are on a weight basis.

EXAMPLE 1

Tests using 250 mg gelatin capsules filled with 240 mg L acidophilus and 10 mg of silicon dioxide are conducted. The capsules are enterically coated with Eudragit polymer and put in a vacuum chamber for 72 hours. The capsules are then held at a range of temperature of 10° C. to 37° C. and a controlled humidity level of 35–40%. The bacterial sample from which the culture in the capsules is taken is prepared with 1,310,000,000 colonies/gram and is not exposed to the above-mentioned temperature and humidity levels. At the end of the first month there are 83 million colonies/capsule. At the end of the second month there are 23 million colonies/capsule. At the end of the third month there are 130 million colonies/capsule. At the end of the fourth month there are 100,000 colonies/capsule. Thus, it can be seen that the culture is still effective after 3 months (the 100,000 colonies/capsule at the end of the fourth month being too low to be effective) at elevated temperature and humidity levels. These results would indicate the effectiveness of the culture at ambient conditions for 12 months; far exceeding the usual shelf life of 7 days of the culture at ambient conditions.

EXAMPLE 2

Capsules are composed of 90% L. acidophilus mixed with 10% silicon dioxide with a fill weight of 200 mg. The cultures used to fill the capsules are taken from a bacterial sample containing 1 billion colonies/gram. The capsules are coated with Sureteric polymer, which is applied by using a liquid bed enteric coat manufacturing process, and are put into a vacuum chamber for 72 hours. The capsules are held at room temperature for one year. The bacterial colony counts after one year is 33 million colonies/gram.

EXAMPLE 3

A study was conducted where 10 patients with lactase deficiency were enrolled in a week-long study. Gelatin capsules containing 90% *L acidophilus* mixed with 10% silicon dioxide were used. The capsules were hand-filled with the mixture, banded, and coated with a 10% Sureteric enteric coating (a polymer of polyvinylacetatephthalate developed by the Canadian subsidiary of Merck & Company). Samples were acid-tested by exposing the coating to 1N HCL for one hour in order to simulate the acid environment of the stomach which resulted in no failures. The capsules were then put in a vacuum chamber for 72 hours.

Two 500 mg capsules were administered to each patient prior to the first meal in the morning each day of the test. The patients were instructed to eat all kinds of food without abstaining from those that were known to cause distress, e.g., bloating, diarrhea, and cramps. Results showed no symptoms of distress while on medication. The significance of this study was that it indicated that this medication was capable of preventing bloating, diarrhea, and cramps caused by foods containing lactose when given to patients. In addition, the study showed that a small sample would last at least for ten hours.

EXAMPLE 4

A study was also conducted where 17 patients with lactase deficiency were enrolled. Consent forms and explanations were given on an individual basis. For one day, each patient was instructed to take two 250 mg gelatin capsules containing 95% *L aciclophilus* and 5% silicon dioxide before breakfast and to eat normally. (These capsules were prepared in the same manner as the capsules described in Example 2.) Each patient was also told to take 50 mg of a "lactose challenge" just before their noon meal. A lactose challenge is equivalent to four ice cream cones or five 10 oz. glasses of milk taken simultaneously. (In clinical test settings, the usual challenge is 20 gm of lactose.) The purpose of the lactose challenge is to determine whether or not the medication would stop any distress when a patient eats or drinks a large amount of lactose. The results were that one patient was disqualified because she was ill prior to beginning the test. For the single-day test, ten out of ten patients tested had mild or no symptoms of bloating or diarrhea after their meals or lactose challenge. The significance of this result was that the medication provides lactose protection even when a patient eats or drinks an enormous amount of lactose.

In a related study, six patients with severe lactase deficiency were given the same 250 mg capsules prepared as described above, two capsules to be taken daily before breakfast, for four to six days. The 50 gm lactose challenge, as described above, was given after four days. The results were that five out of the six patients had no distress during their meals or during the challenge. One patient had diarrhea and cramps after the four days. These results indicate that (1) all patients tolerate a lactose-containing diet utilizing two 250 mg capsules of the medication taken once per day; (2) patients tolerate a lactose challenge of up to 50 gm of lactose in mild to moderate cases of lactase deficiency; and (3) patients with severe cases of lactase deficiency who are given a 50 gm lactose challenge require three to five days to build up a lactase level and are then able to tolerate large doses of lactose at once without symptoms, thus indicating the efficacy of the product under the most challenging conditions.

The present invention may be embodied in other specific forms without departing from the spirit or essential attributes thereof and accordingly, reference should be made to the appended claims rather than to the foregoing specification as indicating the scope of the invention.

I claim:

1. A preparation containing lactase for supplying lactase to mammals having a lactase deficiency which comprises:

an encapsulated stabilized dried bacterial culture containing lactase of a unit dosage amount having a bacterial colony count of at least 250,000, said stabilized dried bacterial culture being a mixture of a dried bacterial culture containing lactase and an amount of a desiccant sufficient to stabilize water content of the dried bacterial culture, said encapsulated stabilized dried bacterial culture being sealed with a polymeric enteric coating and treated under vacuum for a time sufficient to substantially remove oxygen and moisture content thereof and provide desired lactase activity for at least about 10 hours after ingestion.

2. The preparation containing lactase as claimed in claim 3, wherein said bacterial culture containing lactase is selected from the group consisting of bacterial cultures containing *Lactobacillus acidophillus, Lactobacillus bulgaricus, Streptococcus thermophilus,* and mixtures thereof.

3. The preparation containing lactase as claimed in claim 1, wherein said bacterial culture containing lactase comprises bacterial cultures containing *Lactobacillus acidophillus*.

4. The preparation containing lactase as claimed in claim 1 wherein said enteric coated encapsulated stabilized dried bacterial culture is treated under a vacuum pressure for a time sufficient to permit a shelf-life of said culture of at least one year.

5. The preparation containing lactase as claimed in claim 1 wherein said dried bacterial culture is in freeze dried form.

6. A method of preparing a lactase-containing preparation suitable for use by mammals having acquired lactase deficiency comprising the steps of:

a) mixing a dried bacterial culture containing lactase with an amount of a desiccant sufficient to stabilize water content of the dried bacterial culture to produce a stabilized dried bacterial culture;

b) encapsulating a unit dosage amount having a bacterial colony count of at least 250,000 of the stabilized dried bacterial culture produced in step a) in a human or animal ingestible capsule to obtain an encapsulated stabilized dried bacterial culture; and c) sealing the encapsulated stabilized dried bacterial culture from step b) with a polymeric enteric coating to produce an enteric coated encapsulated stabilized dried bacterial culture; and d) treating the enteric coated encapsulated stabilized dried bacterial culture from step c) under a vacuum pressure for a time sufficient to substantially remove oxygen and moisture therefrom and provide desired lactase activity for at least about 10 hours after ingestion.

7. The method of preparing a preparation containing lactase as claimed in claim 6 wherein said enteric coated encapsulated stabilized dried bacterial culture is treated under a vacuum pressure for a time sufficient to permit a shelf-life of said culture of at least one year.

8. The method of preparing a preparation containing lactase as claimed in claim 6 wherein said dried bacterial culture is in freeze dried form.

* * * * *